(12) United States Patent
Yamaguchi

(10) Patent No.: US 8,965,474 B2
(45) Date of Patent: Feb. 24, 2015

(54) TISSUE IMAGING SYSTEM AND IN VIVO MONITORING METHOD

(75) Inventor: Hiroshi Yamaguchi, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 0 days.

(21) Appl. No.: 13/464,393

(22) Filed: May 4, 2012

(65) Prior Publication Data

US 2012/0289801 A1 Nov. 15, 2012

(30) Foreign Application Priority Data

May 12, 2011 (JP) ................................. 2011-107466

(51) Int. Cl.
| | | |
|---|---|---|
| *A61B 5/1455* | (2006.01) | |
| *A61B 1/06* | (2006.01) | |
| *A61B 5/00* | (2006.01) | |
| *A61B 5/1459* | (2006.01) | |
| *A61B 1/00* | (2006.01) | |
| *A61B 1/313* | (2006.01) | |

(52) U.S. Cl.
CPC .............. *A61B 1/063* (2013.01); *A61B 1/0638* (2013.01); *A61B 1/0653* (2013.01); *A61B 5/0075* (2013.01); *A61B 5/14551* (2013.01); *A61B 5/1459* (2013.01); *A61B 1/00009* (2013.01); *A61B 1/0005* (2013.01); *A61B 1/0646* (2013.01); *A61B 1/3132* (2013.01)
USPC ............ 600/323; 600/310; 600/322; 600/324

(58) Field of Classification Search
USPC ................................................. 600/309–344
See application file for complete search history.

(56) References Cited

U.S. PATENT DOCUMENTS

| | | | |
|---|---|---|---|
| 5,001,556 A * | 3/1991 | Nakamura et al. .............. | 348/70 |
| 5,408,998 A | 4/1995 | Mersch | |
| 6,757,555 B2 * | 6/2004 | Kohayakawa ................. | 600/318 |
| 2002/0161291 A1* | 10/2002 | Kianl et al. .................... | 600/324 |

(Continued)

FOREIGN PATENT DOCUMENTS

| | | |
|---|---|---|
| JP | 1-315715 A | 12/1989 |
| JP | 6-285050 A | 10/1994 |

(Continued)

OTHER PUBLICATIONS

Spectros, "T-Stat Ischemia Detection", Real-Time Tissue Perfusion Monitors found Nov. 12, 2010 Spectros Corporation.

(Continued)

*Primary Examiner* — Eric Winakur
*Assistant Examiner* — Marjan Fardanesh
(74) *Attorney, Agent, or Firm* — Birch, Stewart, Kolasch & Birch, LLP

(57) ABSTRACT

An in vivo monitoring method in a laparoscope system is provided. An object image is sequentially created with expression of a surface color of an object in a body cavity. A lock area (specific area) is determined within the object image, the lock area being movable by following motion of the object. A monitor image including a graph of oxygen saturation is generated according to a part image included in the object image and located in the lock area. The monitor image is displayed. Preferably, the oxygen saturation of the lock area is acquired according to two spectral data with respect to wavelengths of which an absorption coefficient is different between oxidized hemoglobin and reduced hemoglobin in data of the object image. The object is constituted by a blood vessel.

16 Claims, 14 Drawing Sheets

(56) References Cited

U.S. PATENT DOCUMENTS

2010/0286475 A1* 11/2010 Robertson ................... 600/104
2011/0077462 A1    3/2011 Saitou et al.

FOREIGN PATENT DOCUMENTS

| | | |
|---|---|---|
| JP | 10-216080 A | 8/1998 |
| JP | 2000-139947 A | 5/2000 |
| JP | 2003-115052 A | 4/2003 |
| JP | 2005-95634 A | 4/2005 |
| JP | 2006-191989 A | 7/2006 |
| JP | 2008-250999 A | 10/2008 |
| JP | 2010-005056 A | 1/2010 |
| JP | 2011-087906 A | 5/2011 |
| WO | WO 2010/134512 A1 | 11/2010 |

OTHER PUBLICATIONS

Notice of Reasons for Refusal issued in corresponding Japanese Patent Application No. 2011-107466 on May 7, 2014, along with an English translation thereof.

Communication pursuant to Article 94(3) EPC issued in corresponding EP Application No. 12165966.8 on Jul. 3, 2014.

* cited by examiner

TISSUE IMAGING SYSTEM AND IN VIVO MONITORING METHOD

BACKGROUND OF THE INVENTION

1. Field of the Invention

The present invention relates to a tissue imaging system and in vivo monitoring method. More particularly, the present invention relates to a tissue imaging system and in vivo monitoring method in which oxygen saturation of body tissue in a body cavity is monitored with high stability even upon incidental shift of a field of view of an imaging instrument for imaging of by body tissue.

2. Description Related to the Prior Art

JP-A 2000-139947 discloses percutaneous treatment (laparoscopic surgery) of a patient's body by use of a laparoscope. In the percutaneous treatment, two or three holes are formed in skin outside an abdominal cavity. The laparoscope and a medical instrument for operation are inserted in the holes into the abdominal cavity. The abdominal cavity is insufflated with gas, such as carbon dioxide gas. A doctor or operator observes an image in the abdominal cavity by use of a monitor display panel, and carries out the percutaneous treatment by use of the medical instrument. The percutaneous treatment is characterized in that the view of field of imaging in the laparoscope is limited considerably, so that the doctor or operator must have a high technical skill. There is an advantage in the percutaneous treatment in that physical stress to the patient is very low, because it is unnecessary to incise the abdominal cavity surgically.

A low oxygen environment is likely to occur with blood vessels in the abdominal cavity because carbon dioxide gas is used in the percutaneous treatment for insufflating the abdominal cavity. In case of the low oxygen environment, the percutaneous treatment is interrupted to start surgical operation. It is necessary in the percutaneous treatment to monitor an oxygen saturation in blood of the blood vessels.

Various methods of monitoring the oxygen saturation are known. In a first one of the methods, a measurement probe is held manually with fingers of a doctor or operator, and measures the oxygen saturation percutaneously. A second one of the methods is disclosed in a relevant website, http://www.spectros.com/products/t-stat-ischemia-detection/about-t-stat/system-overview.html (found on 12 Nov. 2010) in which a non-contact measurement probe is advanced through an instrument channel in the laparoscope, and measures the oxygen saturation of the blood vessels in a non-contact manner. The non-contact measurement probe applies measuring light of a predetermined wavelength to the blood vessels, and receives the light reflected by the blood vessels by use of a CCD image sensor or the like. The image sensor generates an image signal according to which the oxygen saturation of the blood vessels is determined.

Specifically in an artery bypass operation in the percutaneous treatment, it is possible in the non-contact measurement probe of the above-indicated relevant website to monitor changes in the oxygen saturation with time of the blood vessels important surgically (for example, aorta and coronary artery), for the purpose of safety in the percutaneous treatment. However, the above-indicated relevant website discloses measurement in a protruding state of the non-contact measurement probe from a tip of the laparoscope. Should motion occur with the tip of the laparoscope incidentally or in the course of the treatment, there occurs a shift in the position of the non-contact measurement probe. Measuring light from the non-contact measurement probe cannot be sufficiently applied to the blood vessels to be monitored upon occurrence of the shift of the non-contact measurement probe. The oxygen saturation of the blood vessels cannot be exactly determined due to the incidental shift of the non-contact measurement probe.

SUMMARY OF THE INVENTION

In view of the foregoing problems, an object of the present invention is to provide a tissue imaging system and in vivo monitoring method in which oxygen saturation of body tissue in a body cavity is monitored with high stability even upon incidental shift of a field of view of an imaging instrument for imaging of by body tissue.

In order to achieve the above and other objects and advantages of this invention, a tissue imaging system includes an imaging unit for creating an object image of an object with information of oxygen saturation of a blood vessel. An area determining unit determines a specific area within the object image, the specific area being movable by following motion of the object. A monitor image generating unit generates a monitor image including change information of the oxygen saturation according to a part image included in the object image and located in the specific area. A display unit displays the monitor image.

Furthermore, a location updating unit updates a location of the specific area according to the motion of the object at each time of creating a frame of the object image. A data acquisition unit acquires the oxygen saturation of the part image in the specific area when the specific area is updated. The monitor image generating unit generates a graph of the oxygen saturation changeable with time, and the monitor image includes the graph.

The location updating unit extracts a landmark point in relation to the object at each time of creating a frame of the object image, and updates the location of the specific area according to the landmark point.

The object is constituted by a blood vessel, and the landmark point is extracted from a form of the blood vessel.

The location updating unit determines a shift between plural frames of the object image created with a time difference, and updates the location of the specific area according to the shift.

The object image created by the imaging unit is two spectral images of wavelength components of light of which an absorption coefficient is different between oxidized hemoglobin and reduced hemoglobin, and the data acquisition unit acquires the oxygen saturation of the specific area according to the two spectral images.

The display unit displays a currently created frame of the object image within the monitor image together with the graph.

Furthermore, an alarm device generates an alarm signal if the oxygen saturation in the specific area becomes equal to or lower than a predetermined level.

Furthermore, an illumination apparatus applies narrow band light of a predetermined wavelength range and broad band light of a broad wavelength range alternately to the object. The imaging unit is a color image sensor for imaging the object illuminated with the narrow band light and the broad band light.

In another preferred embodiment, furthermore, an illumination apparatus applies plural narrow band light components of wavelength ranges different from one another to the object successively one after another. The imaging unit is a monochromatic image sensor for imaging the object illuminated with the narrow band light components.

The object is present in an abdominal cavity, and the imaging unit is a laparoscope.

In another preferred embodiment, the object is present in a gastrointestinal tract, and the imaging unit is an endoscope.

Also, an in vivo monitoring method is provided, and includes a step of sequentially creating an object image with expression of a surface color of an object in a body cavity. A specific area is determined within the object image, the specific area being movable by following motion of the object. A monitor image including change information of oxygen saturation is generated according to apart image included in the object image and located in the specific area. The monitor image is displayed.

Furthermore, a location of the specific area is updated according to the motion of the object at each time of creating a frame of the object image. The oxygen saturation of the part image in the specific area is acquired when the specific area is updated. The monitor image includes a graph of the oxygen saturation changeable with time.

In the acquiring step, the oxygen saturation of the specific area is acquired according to two spectral data with respect to wavelengths of which an absorption coefficient is different between oxidized hemoglobin and reduced hemoglobin in data of the object image.

Also, a user interface for tissue imaging is provided, and includes an imaging region for sequentially creating an object image with expression of a surface color of an object in a body cavity. A specific area is determined within the object image, and movable by following motion of the object. A generating region is for generating a monitor image including change information of oxygen saturation according to a part image included in the object image and located in the specific area. A displaying region is for displaying the monitor image.

Also, a computer executable program for tissue imaging is provided, and includes an imaging program code for sequentially creating an object image with expression of a surface color of an object in a body cavity. A determining program code is for determining a specific area within the object image, the specific area being movable by following motion of the object. A generating program code is for generating a monitor image including change information of oxygen saturation according to a part image included in the object image and located in the specific area. A displaying program code is for displaying the monitor image.

Consequently, oxygen saturation of body tissue in a body cavity is monitored with high stability even upon incidental shift of a field of view of an imaging instrument for imaging of by body tissue, because a lock area of an object image is utilized to follow the motion of an object of interest.

BRIEF DESCRIPTION OF THE DRAWINGS

The above objects and advantages of the present invention will become more apparent from the following detailed description when read in connection with the accompanying drawings, in which.

DETAILED DESCRIPTION OF THE PREFERRED EMBODIMENT(S) OF THE PRESENT INVENTION

Figure 1:
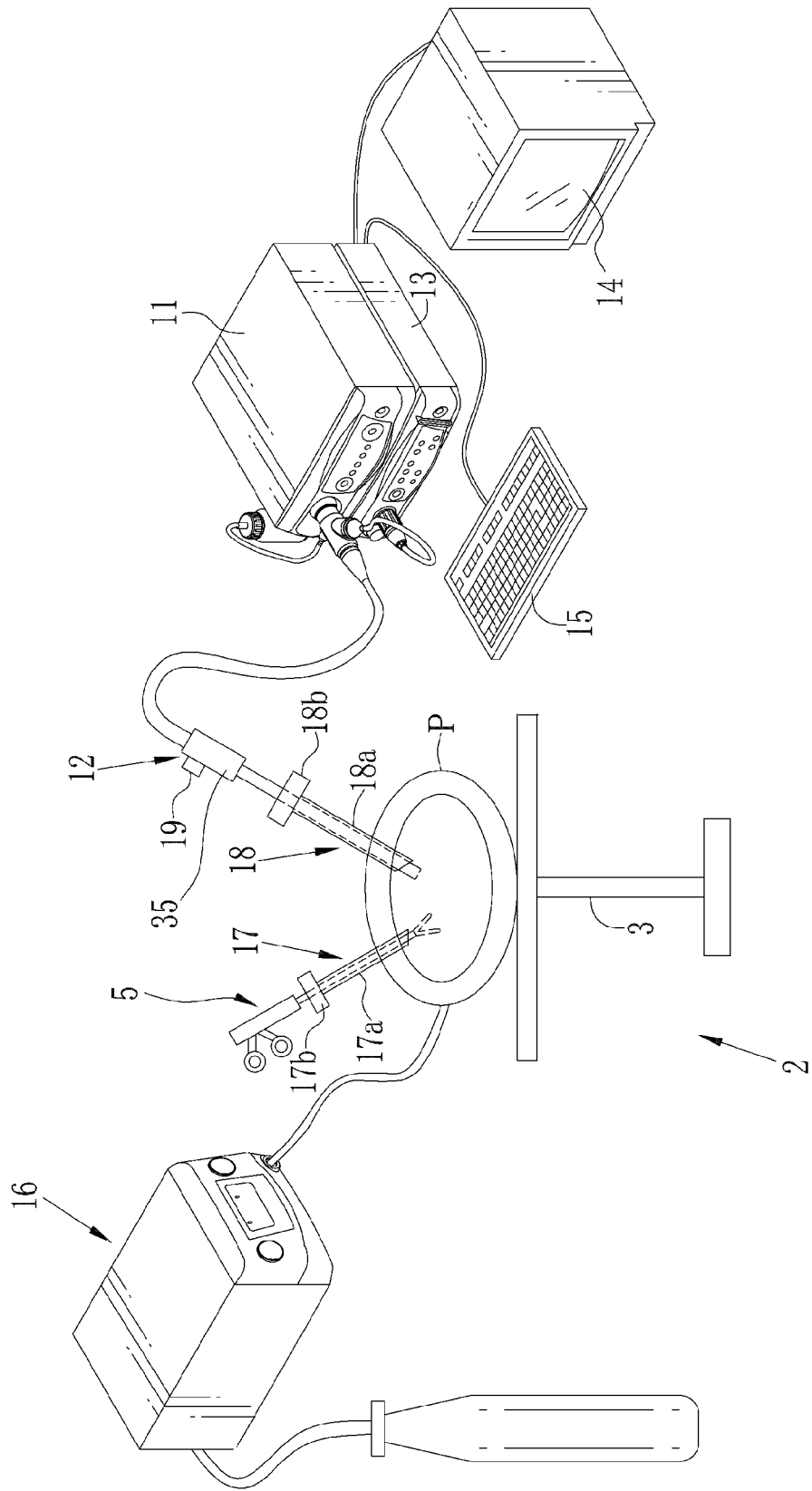
FIG. 1 is an explanatory view illustrating a laparoscope system.

In FIG. 1, a laparoscope system 2 as tissue imaging system is illustrated. A body of a patient P lies on an operating table 3. A laparoscope 12 is entered in a body cavity of the body for imaging body tissue as a target of percutaneous treatment (laparoscopic surgery). An electrocautery device 5 or other medical instruments are used for the treatment. The laparoscope system 2 includes an illumination apparatus 11, the laparoscope 12, a processing apparatus 13 and a display panel 14 as display unit. The illumination apparatus 11 emits light of a predetermined wavelength range. The laparoscope 12 has optics for guiding the light to the body tissue, and also detects object light reflected by the body tissue. The processing apparatus 13 processes an image signal from the laparoscope 12. The display panel 14 displays the image after the image processing. An insufflator 16 supplies the body cavity with carbon dioxide gas for maintaining a space for viewing and treatment.

Trocars 17 and 18 guide the electrocautery device 5 and the laparoscope 12 for entry in the body cavity. The trocar 17 includes a trocar sleeve 17a of metal and a manually operable trocar housing 17b. The trocar 18 includes a trocar sleeve 18a of metal and a manually operable trocar housing 18b. A doctor or operator percutaneously enters tips of the trocar sleeves 17a and 18a into a body by grasping the trocar housings 17b and 18b, so as to advance the trocar sleeves 17a and 18a into the body. The electrocautery device 5 and the laparoscope 12 are entered into the body through the trocars 17 and 18 while guided by the trocar sleeves 17a and 18a.

The laparoscope system 2 operates in plural modes including a normal imaging mode and a monitor mode. In the normal imaging mode, the display panel 14 displays a normal image of an object with visible light of wavelengths from blue to red. In the monitor mode, oxygen saturation of body tissue is monitored with time, the body tissue including blood vessels, which are medically important for artery bypass operation or the like. The laparoscope 12 includes a selection switch 23. The modes are selectively set in response to a control signal generated by the selection switch 23 or an input interface 15 connected externally.

Figure 2:
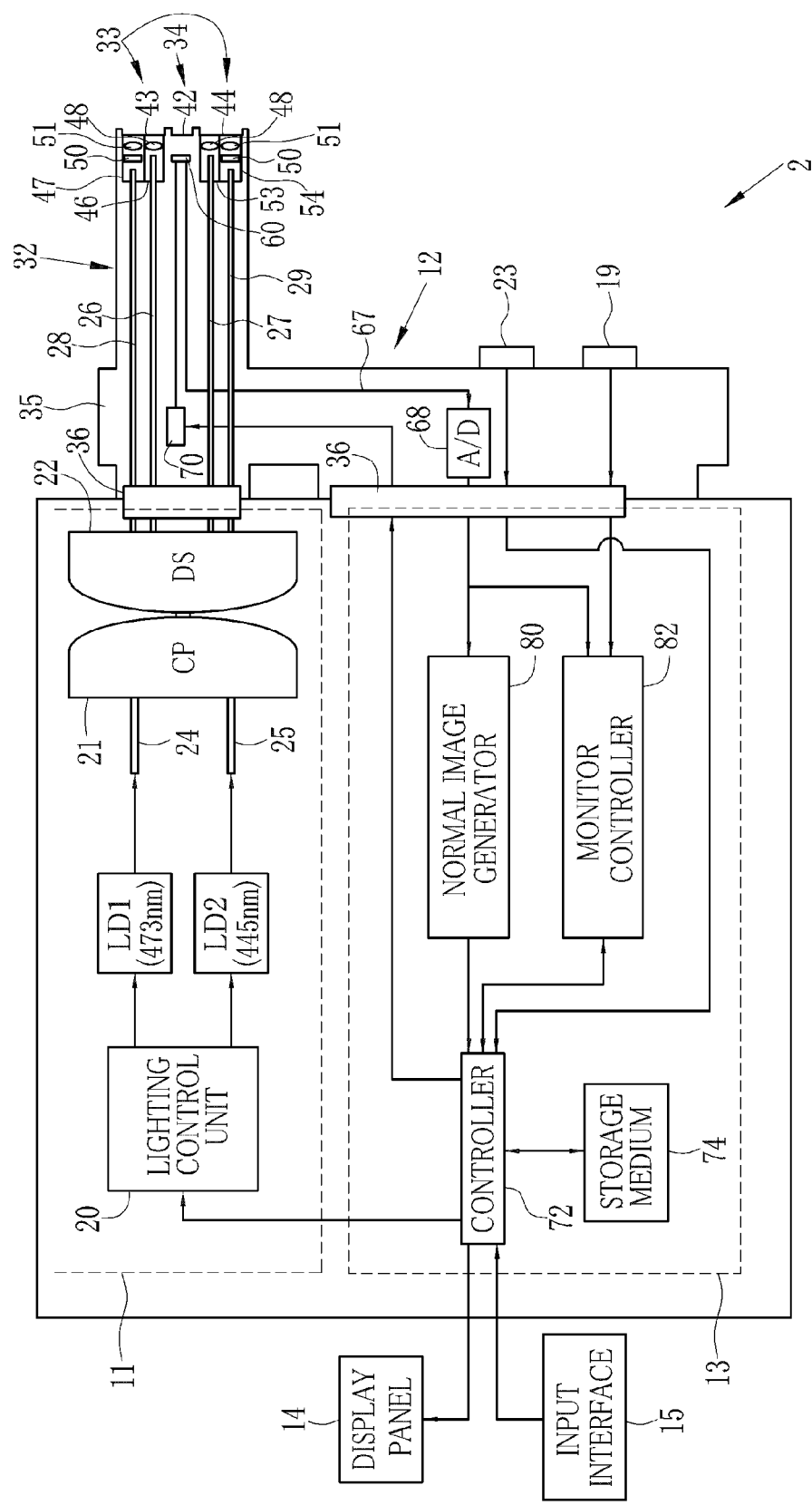
FIG. 2 is a block diagram illustrating the laparoscope system.

In FIG. 2, the illumination apparatus 11 includes two laser light sources LD1 and LD2, a lighting control unit 20, an optical coupler (CP) 21 and an optical distributor (DS) 22. The laser light source LD1 generates narrow band light for measuring oxygen saturation, which is hereinafter referred to as measuring light. A center wavelength of the measuring light is 473 nm. Phosphor 50 is disposed at a distal end of the laparoscope 12. The laser light source LD2 generates excitation light, which is incident upon the phosphor 50 which emits white light or pseudo white light by excitation. A center wavelength of the excitation light is 445 nm.

Condenser lenses (not shown) condense light from the laser light sources LD1 and LD2. There are fiber optics 24 and 25 upon which the condensed light is incident. Examples of the laser light sources LD1 and LD2 include InGaN laser diodes of a broad area type, InGaNAs laser diodes, GaNAs laser diodes and the like.

The lighting control unit 20 controls the laser light sources LD1 and LD2 to adjust their emission sequence and a ratio between their light amounts. In the normal imaging mode of the embodiment, the laser light source LD1 is turned off. The laser light source LD2 is turned on. In the monitor mode, only the laser light source LD1 is turned on while the laser light source LD2 is turned off. Otherwise, only the laser light source LD2 is turned on while the laser light source LD1 is turned off. The operation of their changeover is repeated at each time of a lapse of a predetermined time.

The optical coupler 21 combines light from the fiber optics 24 and 25. The combined light is distributed by the optical distributor 22 to generate light of four light paths. Among those, the light from the laser light source LD1 is transmitted by light guide devices 26 and 27. The light from the laser light source LD2 is transmitted by light guide devices 28 and 29. An example of each of the light guide devices 26-29 is a bundle fiber including a great number of optical fibers. It is possible to introduce the light from the laser light sources LD1 and LD2 directly to the light guide devices 26-29 without use of the optical coupler 21 or the optical distributor 22.

The laparoscope 12 includes a guide tube 32 with a head assembly for imaging, a light emitter 33, an imaging unit 34 or camera head, a handle device 35 and a connector 36. The light emitter 33 emits light from the four light paths in association with the light guide devices 26-29. The imaging unit 34 as a single unit detects object light from an object for imaging. The handle device 35 is manually held, and used for steering of the head assembly of the guide tube 32 and for imaging. The connector 36 connects the guide tube 32 and the illumination apparatus 11 to the processing apparatus 13 in a removable manner.

Two lighting windows 43 and 44 are formed in the light emitter 33 and disposed beside the imaging unit 34, and apply measuring light and white light to an object of interest. An imaging window 42 is formed in the imaging unit 34 at the center of the tip of the guide tube 32, and receives light reflected by the object of interest for imaging.

Two lighting units 46 and 47 are contained in a space behind the lighting window 43. A lens 48 is associated with the lighting unit 46, which emits measuring light from the light guide device 26 through the lens 48 toward an object of interest. Also, a lens 51 is associated with the lighting unit 47, which emits white light created by the phosphor 50 and the light guide device 28, and applies the white light through the lens 51 toward the object of interest. Additionally, two lighting units 53 and 54 are contained in a space behind the lighting window 44. The lighting unit 53 is similar to the lighting unit 46. The lighting unit 54 is similar to the lighting unit 47.

Figure 3:
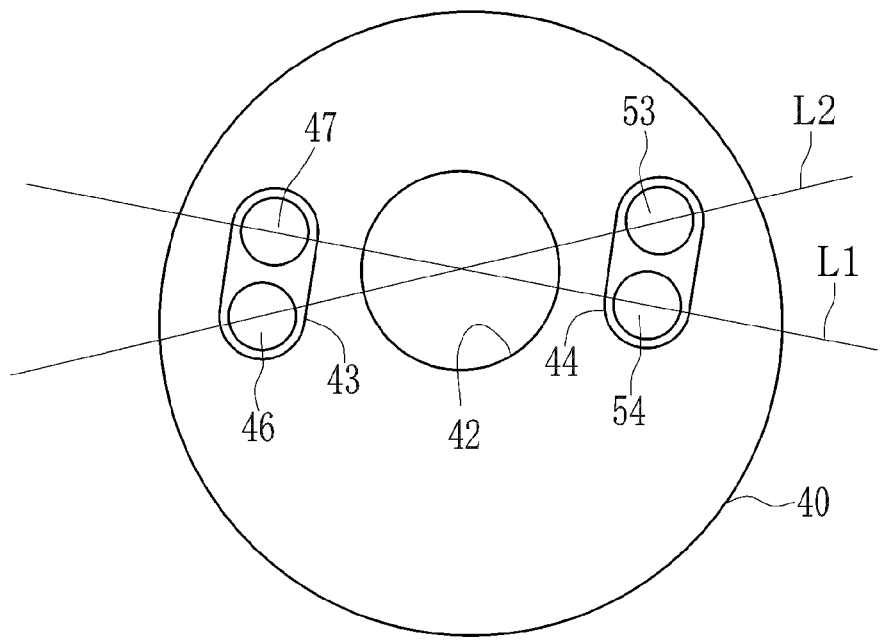
FIG. 3 is a front elevation illustrating a head assembly of the laparoscope system.

The lighting units 46, 47, 53 and 54 are arranged in the manner of FIG. 3. A straight line L1 defined to pass the centers of the lighting units 47 and 54 intersects with a straight line L2 defined to pass the centers of the lighting units 46 and 53 at the center of the imaging window 42. The lighting units 47 and 54 with the phosphor 50 are arranged alternately with the lighting units 46 and 53 without the phosphor 50. This is effective in preventing occurrence in unevenness in the lighting.

The phosphor 50 excites to emit light from green to yellow by partially absorbing excitation light from the laser light source LD2. Examples of compounds included in the phosphor 50 are YAG phosphor, BAM phosphor ($BaMgAl_{10}O_{17}$) and the like. When the excitation light becomes incident upon the phosphor 50, the phosphor 50 applies composite light to body tissue of a body cavity, the composite light being broad band light (pseudo white light) in combination of the fluorescence from green to yellow from the phosphor 50, and the excitation light transmitted by the phosphor 50. An example of the phosphor 50 is Micro White (MW) (trade name) manufactured by Nichia Corporation.

Figure 4:
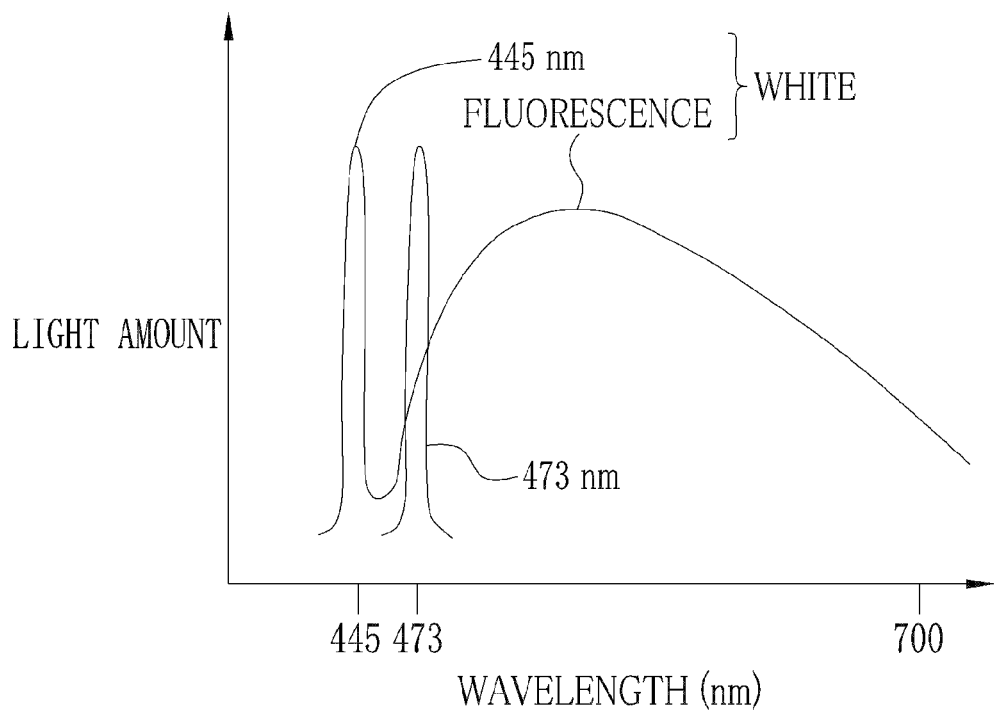
FIG. 4 is a graph illustrating a relationship between oxygen saturation and spectral distribution of white light.

In FIG. 4, spectral intensity of white light from the lighting units 47 and 54 with the phosphor 50 is illustrated. The white light has a component of a wavelength range of excitation light with a center wavelength of 445 nm, and a fluorescent component of a wavelength range of 450-700 nm after the excitation of the excitation light. Measuring light is emitted by the lighting units 46 and 53 without the phosphor 50, and is a component of a wavelength range with a center wavelength of 473 nm.

Note that the white light as broad band light for a technical term in the present invention not only is white light broadly containing all components of visible light, but also can be the pseudo white light described above, light at least containing red, green and blue components as primary colors, and also light containing components from green to red, and light containing components from blue to green.

Plural elements are disposed behind the imaging window 42, including a lens system and an image sensor 60. The lens system (not shown) receives object light from an object. The image sensor 60, for example, CCD (charge coupled device) and CMOS (complementary metal oxide semiconductor), detects the object light for imaging the object.

The image sensor 60 receives light from the lens on its reception surface, and converts the light photoelectrically into a video signal of analog signal. The image sensor 60 is a color CCD and has plural arrays of pixels, namely red pixels of red filters, green pixels of green filters, and blue pixels of blue filters.

Figure 5:
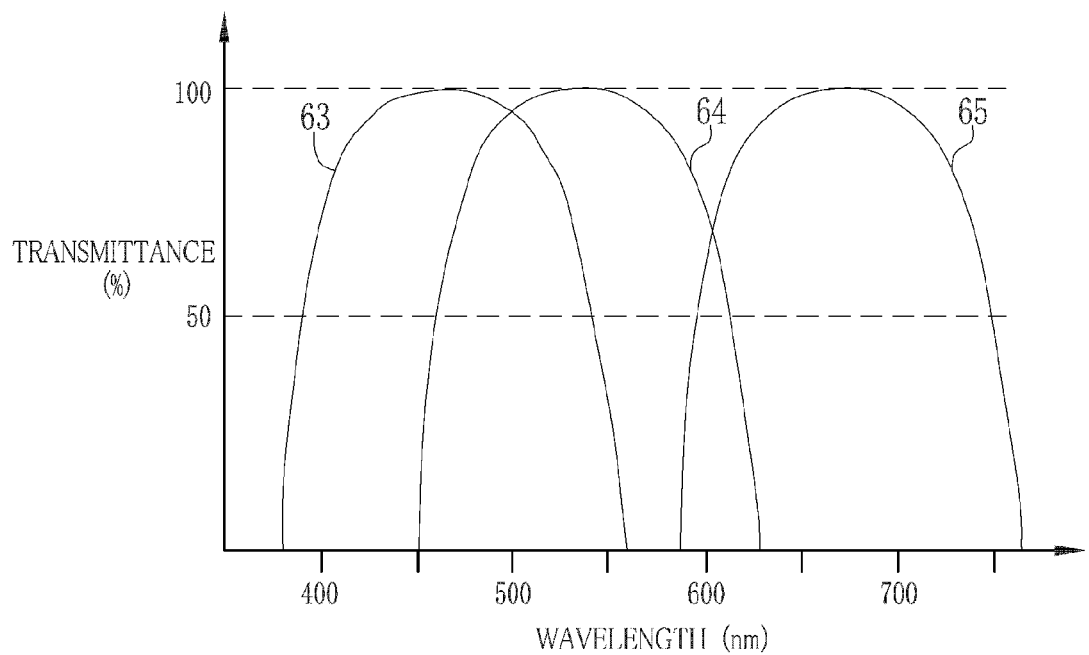
FIG. 5 is a graph illustrating spectral transmittance of red, green and blue filters.

In FIG. 5, spectral transmittance curves 63, 64 and 65 of blue, green and red filters are illustrated. In principle, white light included in light reflected by an object of interest passes all the blue, green and red filters. The image sensor 60 outputs a video signal with luminance equal to or more than a reference luminance in relation to all pixels of blue, green and red.

In contrast, the measuring light has a center wavelength of 473 nm. The image sensor 60 outputs a video signal of blue pixels with luminance equal to or more than a reference luminance, but outputs a video signal of green and red pixels with luminance of zero or very low luminance.

A signal line 67 transmits the video signal (analog) from the image sensor 60. An A/D converter 68 is supplied with the video signal by the signal line 67. The A/D converter 68 converts the video signal into an image signal in a digital form which corresponds to the voltage level of the video signal before the conversion. A normal image generator 80 for a normal image and a monitor controller 82 for oxygen saturation or oxygen saturation monitoring unit are incorporated in the processing apparatus 13, and supplied with the image signal through the connector 36.

Figure 6A:
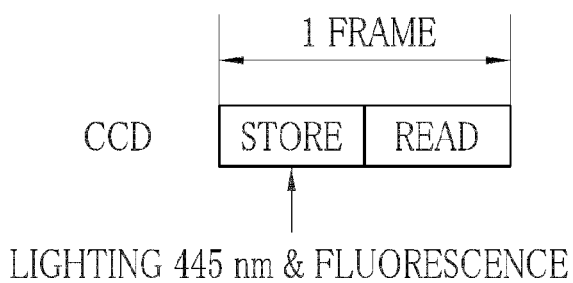
FIG. 6A is a timing chart illustrating control of a CCD in a normal imaging mode.

An imaging control unit 70 controls imaging of the image sensor 60. In FIG. 6A, there are two steps in the normal imaging mode. In a first one of the steps, charge is stored after photoelectric conversion of white light into the charge in one frame time period. In a second one of the steps, the charge is read. Thus, an image signal of the normal image is obtained. The imaging is carried out repeatedly while the normal imaging mode is set. Note that the white light for use is generated by fluorescence upon excitation of light of 445 nm with the phosphor 50.

Figure 6B:
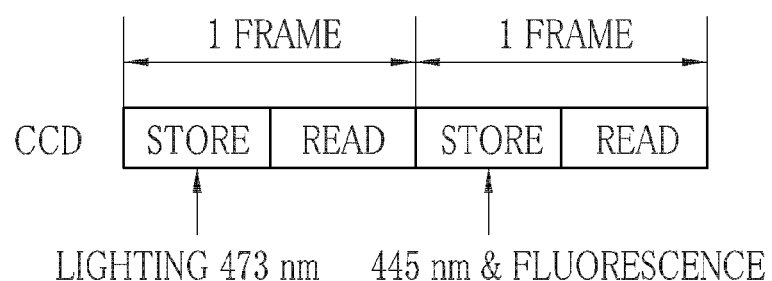
FIG. 6B is a timing chart illustrating control of the CCD in a monitor mode for the oxygen saturation.

In FIG. 6B, a sequence in the monitor mode is illustrated. Operation in a frame time period for a first frame includes a charging step and a reading step. In the charging step, the charge obtained by photoelectric conversion of measuring light of a narrow band of 473 nm is stored. In the reading step, the charge is read. Then operation in a frame time period for a second frame includes a charging step and a reading step. In the charging step, the charge obtained by photoelectric conversion of white light (445 nm with fluorescence) is stored. In the reading step, the charge is read. Thus, an image signal of an evaluation image set is obtained, inclusive of a special light mode image of the first frame and a normal image of the second frame. The sequence according to this control is repeated while the monitor mode is set.

Let B1 be a blue signal output by blue pixels of the image sensor 60 in relation to an image signal of a first frame of a special light mode image. Let G1 and R1 be green and red signals output by green and red pixels of the image sensor 60 in relation to the image signal of the first frame of the special light mode image. Let B2 be a blue signal output by blue pixels of the image sensor 60 in relation to an image signal of a second frame of a special light mode image. Let G2 and R2 be green and red signals output by green and red pixels of the image sensor 60 in relation to the image signal of the second frame of the special light mode image.

In FIG. 2, the processing apparatus 13 includes a controller 72 as display control unit, a storage medium 74, the normal image generator 80 and the monitor controller 82. The display panel 14 and the input interface 15 are connected to the controller 72. The controller 72 controls the normal image generator 80, the monitor controller 82, the lighting control unit 20 in the illumination apparatus 11, the imaging control unit 70 in the laparoscope 12, and the display panel 14 according to control signals from the selection switch 23, a lock-on switch 19 in the laparoscope 12 as lock area determining unit, and the input interface 15.

The normal image generator 80 creates a normal image by image processing of an image signal obtained in the normal imaging mode. The normal image is displayed on the display panel 14.

Figure 7:
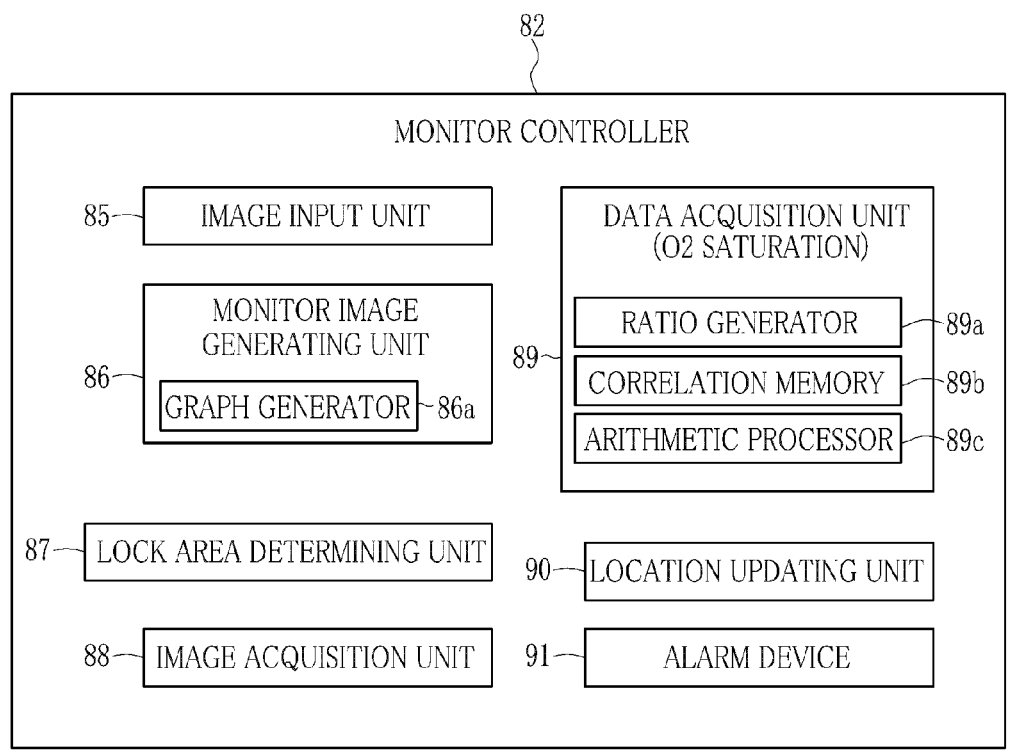
FIG. 7 is a block diagram illustrating a monitor controller for the oxygen saturation.

In the monitor mode, the monitor controller 82 measures changes in the oxygen saturation with time for an object of interest in a body cavity, and monitors a state of oxygen in the object of interest. In FIG. 7, the monitor controller 82 includes an image input unit 85, a monitor image generating unit 86 or image synthesis unit, a lock area determining unit 87 or specific area determining unit (lock-on area determining unit), an image acquisition unit 88, a data acquisition unit 89 for oxygen saturation, a location updating unit 90, and an alarm device 91. The image input unit 85 receives an input of an evaluation image set. The monitor image generating unit 86 creates a monitor image 94 or state image for in vivo monitoring of FIG. 8, which is displayed on the display panel 14 with a current object image and its changes with time. The area determining unit 87 determines a lock area 98 or specific area (lock-on area) of FIG. 9 positioned for tracking motion of an object of interest. The image acquisition unit 88 acquires information of a part image in the lock area 98. The data acquisition unit 89 acquires oxygen saturation of the part image in the lock area 98 according to the acquired image in the image acquisition unit 88. The location updating unit 90 updates the location of the lock area 98 at each time of creating an evaluation image set after determining the lock area. The alarm device 91 emits alarm sound when the oxygen saturation of the lock area 98 becomes lower than a predetermined value.

Figure 8:
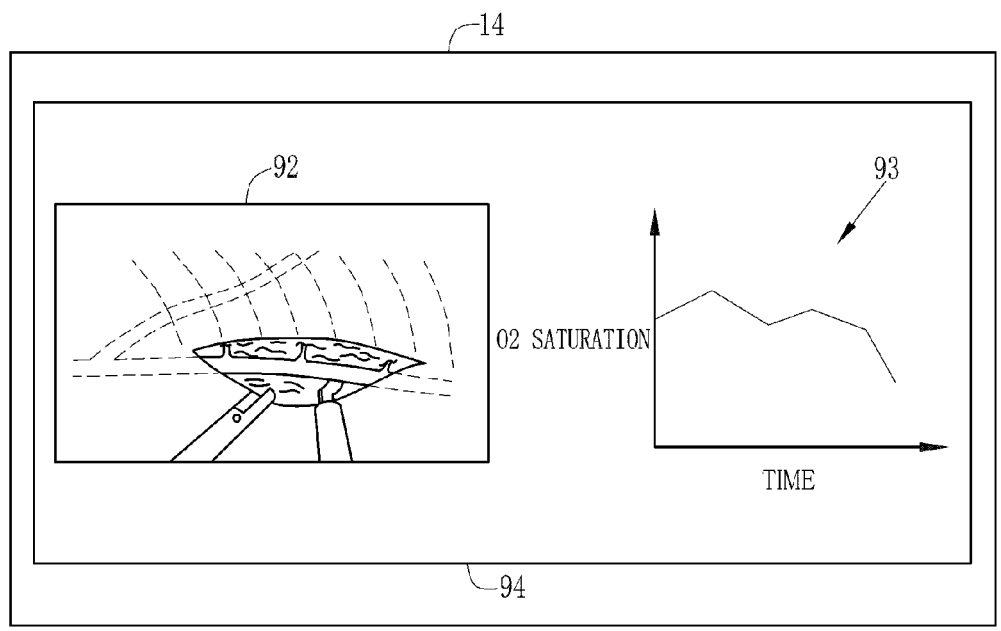
FIG. 8 is an explanatory view illustrating a monitor image.

The image input unit 85 receives an evaluation image set in an order of imaging with the image sensor 60, and sends data of the evaluation image set to the monitor image generating unit 86, the area determining unit 87 and the location updating unit 90. In FIG. 8, the monitor image generating unit 86 creates the monitor image 94 containing an object image 92 and a graph 93. The object image 92 is a current normal image included in the evaluation image set. The graph 93 is disposed beside the object image 92 and represents the oxygen saturation of the body tissue with sequential changes. The monitor image 94 is created at each time that an evaluation image set is created, and at each time that the data acquisition unit 89 acquires the oxygen saturation. The monitor image 94 is displayed on the display panel 14. Note that a graph generator 86a plots values of the oxygen saturation on the graph 93.

Figure 9A:
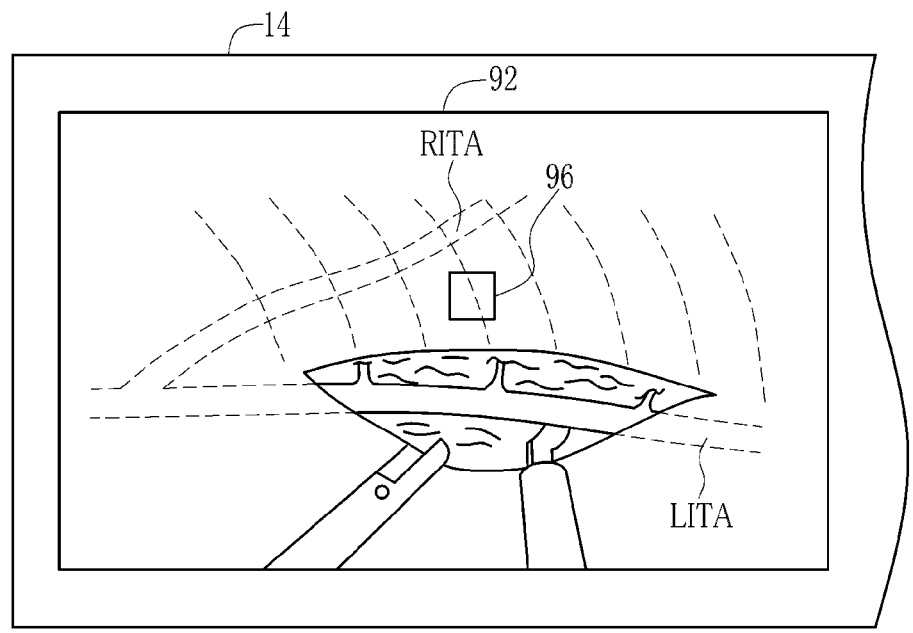
FIG. 9A is an explanatory view illustrating a sequence of determining a lock area.
Figure 9B:
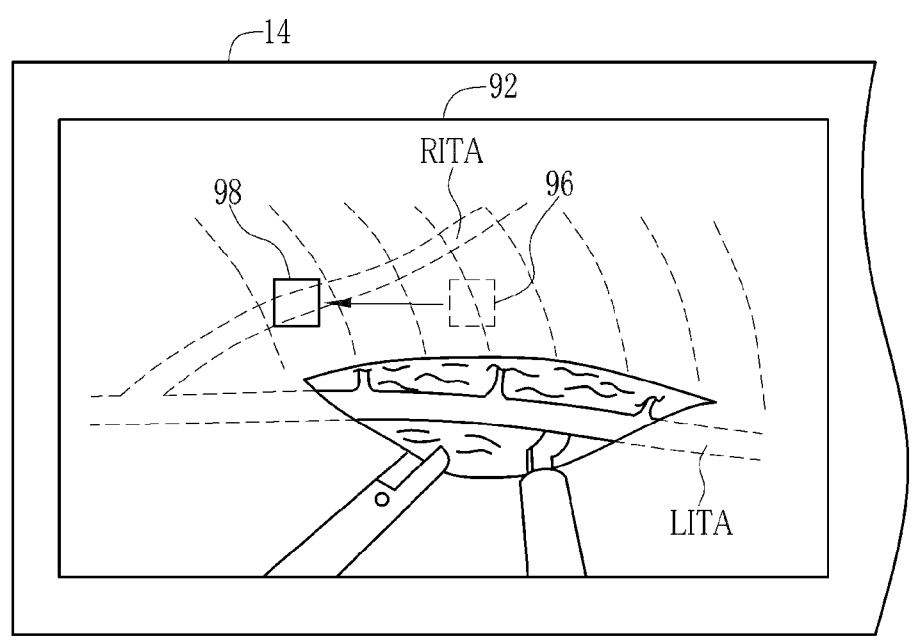
FIG. 9B is an explanatory view illustrating the determined lock area.

In FIG. 9A, a reference area 96 of a quadrilateral shape is indicated by the area determining unit 87 at a predetermined point in the object image 92. A doctor or operator operates the head assembly of the guide tube 32 or the input interface 15 in order to enter an object of interest in the reference area 96. Examples of the object of interest are a right internal thoracic artery or RITA, and a left internal thoracic artery or LITA. The lock-on switch 19 is depressed when the object of interest enters the reference area 96. In FIG. 9B, a region of the object of interest is determined as the lock area 98. Measurement of changes of the oxygen saturation of the lock area 98 with time is started.

After the lock area 98 is determined, image sets are sent to the image acquisition unit 88, including the first evaluation image set (first normal image and first special light mode image), and the second evaluation image set (second normal image and second special light mode image), . . . , and the nth evaluation image set (nth normal image and nth special light mode image). The number n is an integer of 2 or more, and expresses that its time point of imaging is late according to its increase.

Figure 10:
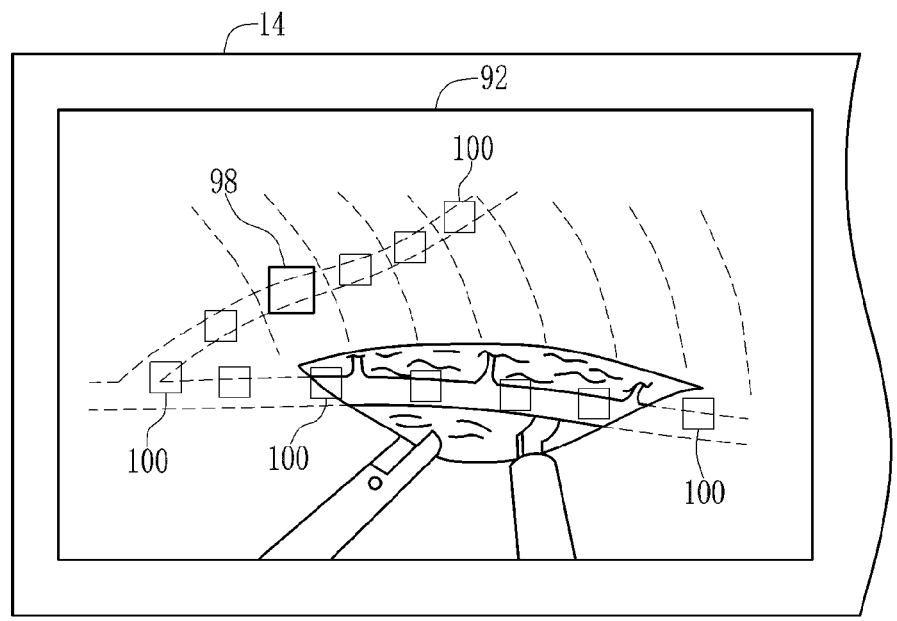
FIG. 10 is an explanatory view illustrating landmark points for setting the lock area.

In FIG. 10, landmark points 100 as marking information are extracted by the image acquisition unit 88 from a first normal image in a first evaluation image set, namely points where a feature value is equal to or more than a predetermined level. The landmark points 100 are used to determine a location of the lock area 98 from an nth evaluation image set which is created after the first evaluation image set. An example of a method of obtaining the feature value of the landmark points 100 is edge detection of blood vessels extending in a body cavity according to a technique of feature detection by image analysis. Examples of body parts for the edge detection are a portion of body tissue on a borderline between vessels and tissue near to the vessels, and a portion of intersection of blood vessels, and the like.

Note that the numeral of 100 in FIG. 10 is indicated only to part of the landmark points 100 for simplicity in the drawing. The extraction of the landmark points 100 is carried out according to a normal image in which body tissue with vessels and the like is imaged clearly. Also, it is possible to extract the landmark points 100 according to a special light mode image in particular when body tissue is imaged clearly.

Also, the image acquisition unit 88 extracts signal levels (blue signal B1', green signal G1' and red signal R1') of the part image of the lock area 98 from the special light mode image in the evaluation image set, and extracts signal levels (blue signal B2', green signal G2' and red signal R2') of the part image of the lock area 98 from the normal image. The extracted signal levels are used for determining oxygen saturation of the body tissue.

In FIG. 7, the data acquisition unit 89 includes a ratio generator 89a, a correlation memory 89b and an arithmetic processor 89c, and determines oxygen saturation of the lock area 98 according to a signal level obtained by the image acquisition unit 88. The ratio generator 89a determines a signal ratio between pixels disposed in equal positions between a special light mode image and a normal image according to an image signal of the part image of the lock area 98. In the embodiment, the ratio generator 89a determines a signal ratio B1'/G2' of the blue signal B1' of the special light mode image to the green signal G2' of the normal image, and a signal ratio R2'/G2' of the red signal R2' of the normal image to the green signal G2' of the normal image.

Figure 11:
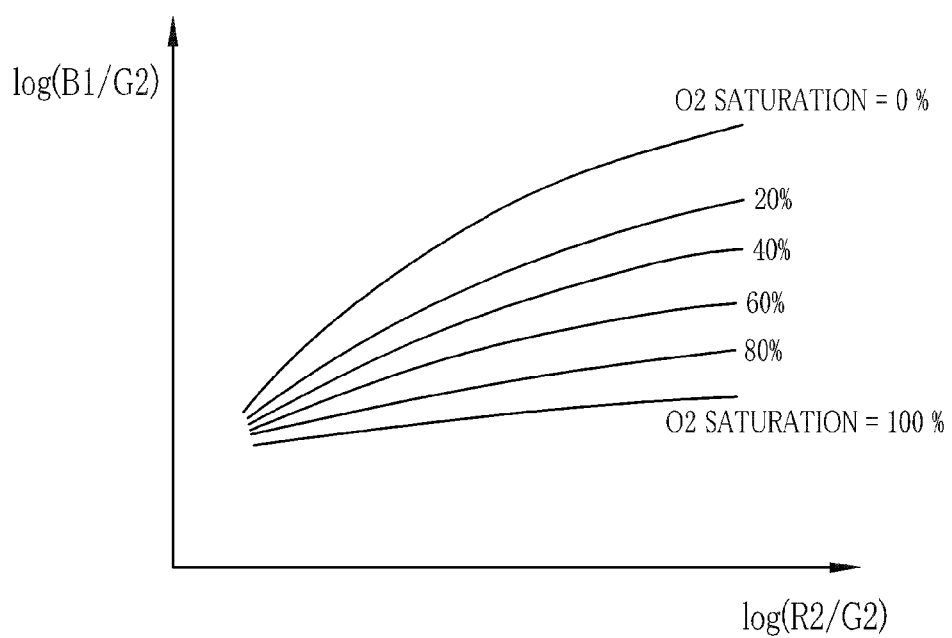
FIG. 11 is a graph illustrating a relationship between the oxygen saturation and signal ratios.

The correlation memory 89b stores information of a correlation between the oxygen saturation and signal ratios B1/G2 and R2/G2 of the total of the image signal obtained in the monitor mode for oxygen saturation. The correlation is expressed by use of a two-dimensional table of FIG. 11 where isolines of oxygen saturation are defined. The position and shape of the isoline is obtained by physical simulation of light scattering, and defined variably according to a blood volume. If a change in the blood volume occurs, an interval between the isoline increases or decreases. Note that the signal ratios B1/G2 and R2/G2 are stored according to the logarithmic scale.

Figure 12:
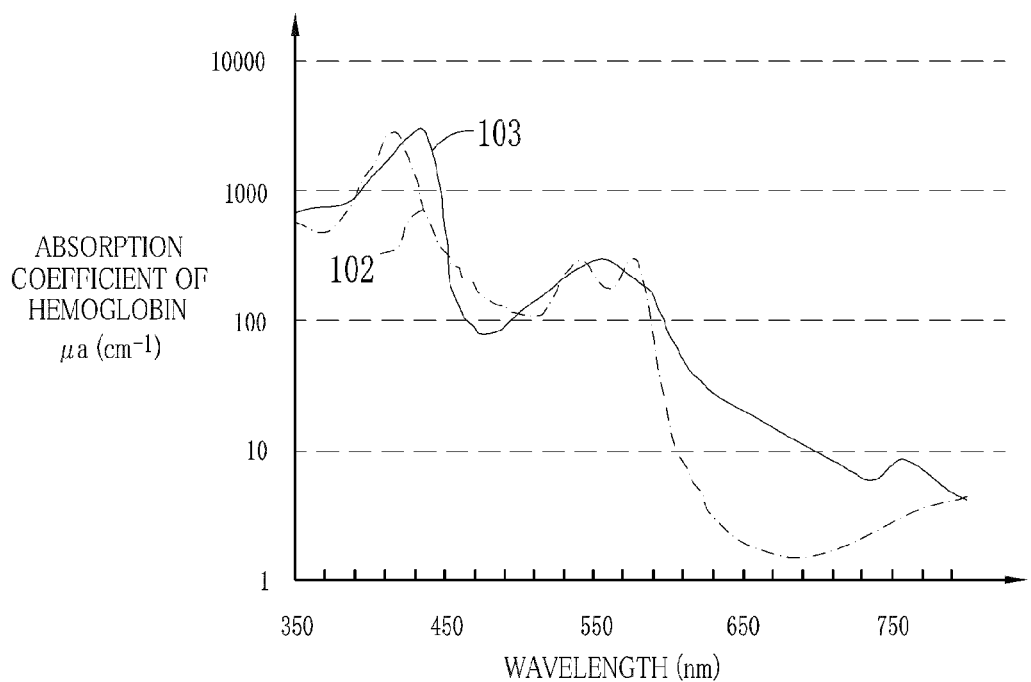
FIG. 12 is a graph illustrating an absorption coefficient of hemoglobin.

The above correlation is relevant closely to characteristics of absorption and light scattering of oxidized hemoglobin and reduced hemoglobin, as illustrated in FIG. 12. A first absorption curve 102 in FIG. 12 represents an absorption coefficient of the oxidized hemoglobin. A second absorption curve 103 represents an absorption coefficient of the reduced hemoglobin. It is easy to acquire information of oxygen saturation at the wavelength of 473 nm where a difference in the absorption coefficient is large. However, the blue signal having a signal component according to light of 473 nm is not only dependent upon oxygen saturation but also dependent upon a blood volume of blood. Thus, signal ratios B1/G2 and R2/G2 are utilized according to the blue signal B1, a red signal R2 of light changing with dependency on the blood volume, and a green signal G2 as a reference for those. It is possible to determine the oxygen saturation precisely in a manner independent from the blood volume.

The absorption coefficient of blood hemoglobin has dependency to the wavelength of light, specifically as follows.

If the wavelength is in a range of 470 nm plus or minus 10 nm (near to 470 nm as center wavelength of blue), the absorption coefficient is changeable greatly according to a change in the oxygen saturation.

If the wavelength is in a range of 540-580 nm of green, the absorption coefficient is not remarkably influenced by the oxygen saturation.

Also, if the wavelength is in a range of 590-700 nm of red, the absorption coefficient is not influenced by the oxygen saturation, because the absorption coefficient is extremely small.

The arithmetic processor 89c determines oxygen saturation in the lock area 98 by use of the correlation read from the correlation memory 89b and the signal ratios B1'/G2' and R2'/G2' obtained by the ratio generator 89a. To this end, at first a coordinate point P corresponding to the signal ratios B1'/G2' and R2'/G2' is determined in a two-dimensional space in FIG. 13.

Figure 13:
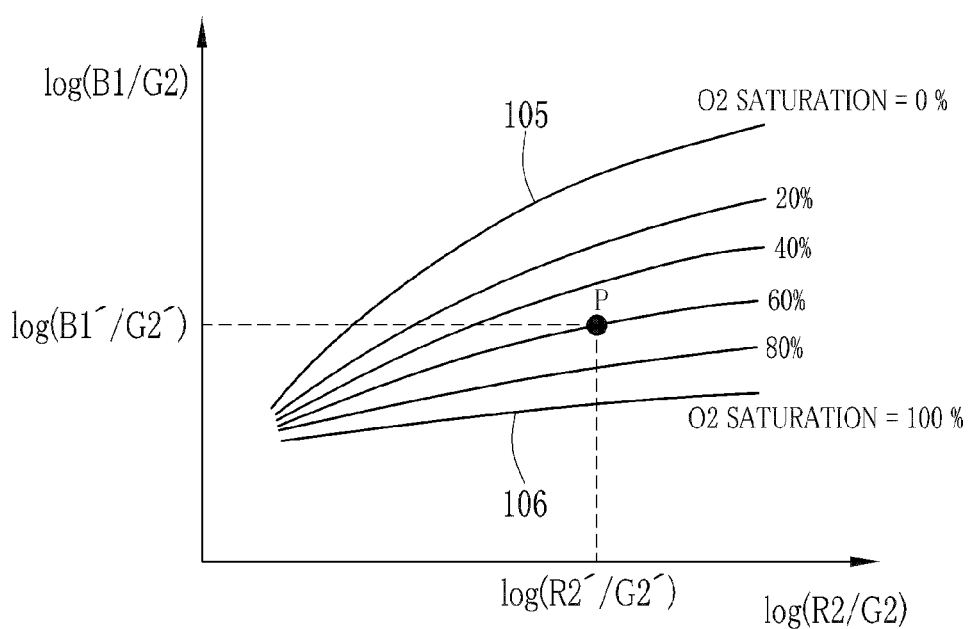
FIG. 13 is a graph illustrating the signal ratios with isolines of the oxygen saturation.

In the drawing, a lower limit 105 is a curve where the oxygen saturation is 0%. An upper limit 106 is a curve where the oxygen saturation is 100%. If the coordinate point P is located between the upper and lower limits 105 and 106, one of the isolines where the coordinate point P is located is specified to read oxygen saturation associated with the isoline. For example, the coordinate point P in FIG. 13 is located on the isoline of 60%. So the oxygen saturation is 60%. Then the graph generator 86a plots the determined oxygen saturation on the graph 93 in the monitor image 94.

The coordinate point P may not be present between the upper and lower limits 105 and 106. If the coordinate point P is located higher than the lower limit 105, then the oxygen saturation is set equal to 0%. If the coordinate point P is located lower than the upper limit 106, then the oxygen saturation is set equal to 100%. Note that if the coordinate point P is not present between the upper and lower limits 105 and 106, it is possible to hide the coordinate point P due to unreliability of oxygen saturation of pixels.

Figure 14A:
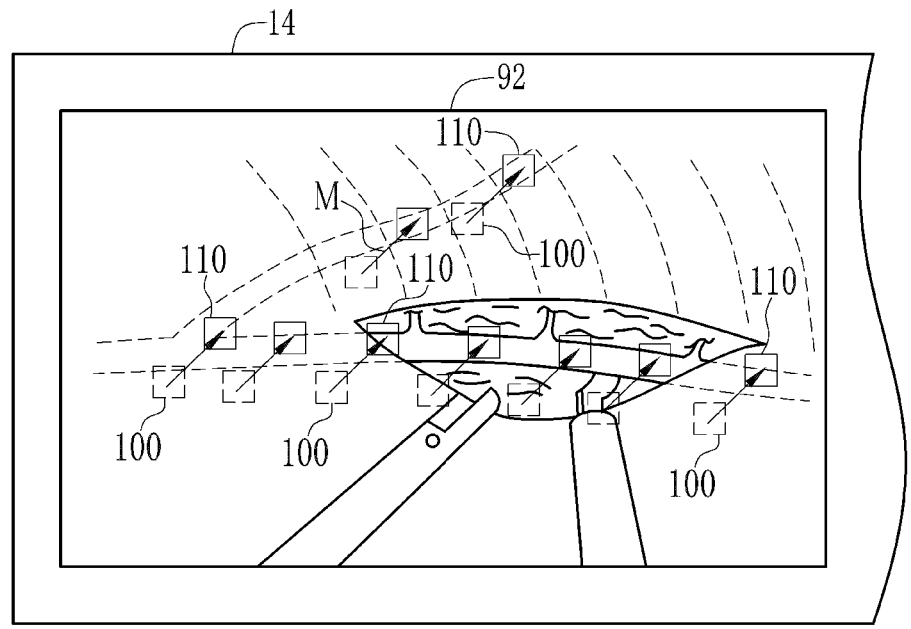
FIG. 14A is a graph illustrating updating of the lock area.

In FIG. 14A, the location updating unit 90 extracts plural landmark points 110 as marking information from an nth normal image included in an nth evaluation image set created after the first evaluation image set. The extraction is the same as that of the landmark points 100 described above. Part of the landmark points 100 in the first normal image and part of the landmark points 110 in the nth normal image, in which the feature value is equal, are specified. Then a movement amount M (or motion vector) between the specified landmark points 100 and 110 is obtained. A shift between the first and nth normal images is obtained according to the movement amount M. Note that only part of the landmark points 100 and 110 in FIG. 14 are designated with the reference numerals for the purpose of simplicity.

Figure 14B:
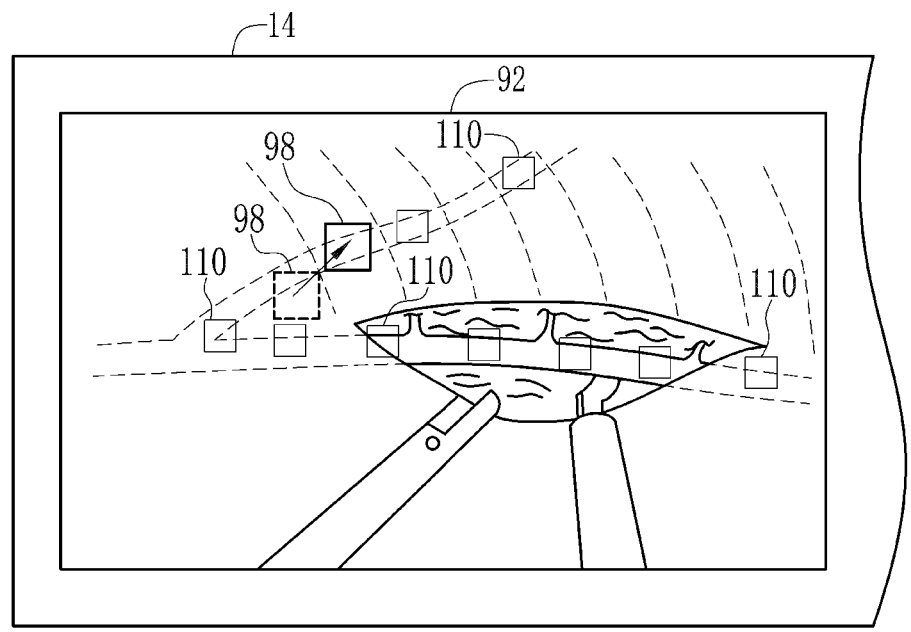
FIG. 14B is a graph illustrating a change in the lock area according to the updating.

In FIG. 14B, the location of the lock area 98 in the nth evaluation image set for measurement changed according to the obtained shift. Thus, the location of the lock area 98 is updated. In response, the oxygen saturation in the lock area 98 is measured again in the same manner as described above.

Figure 15:
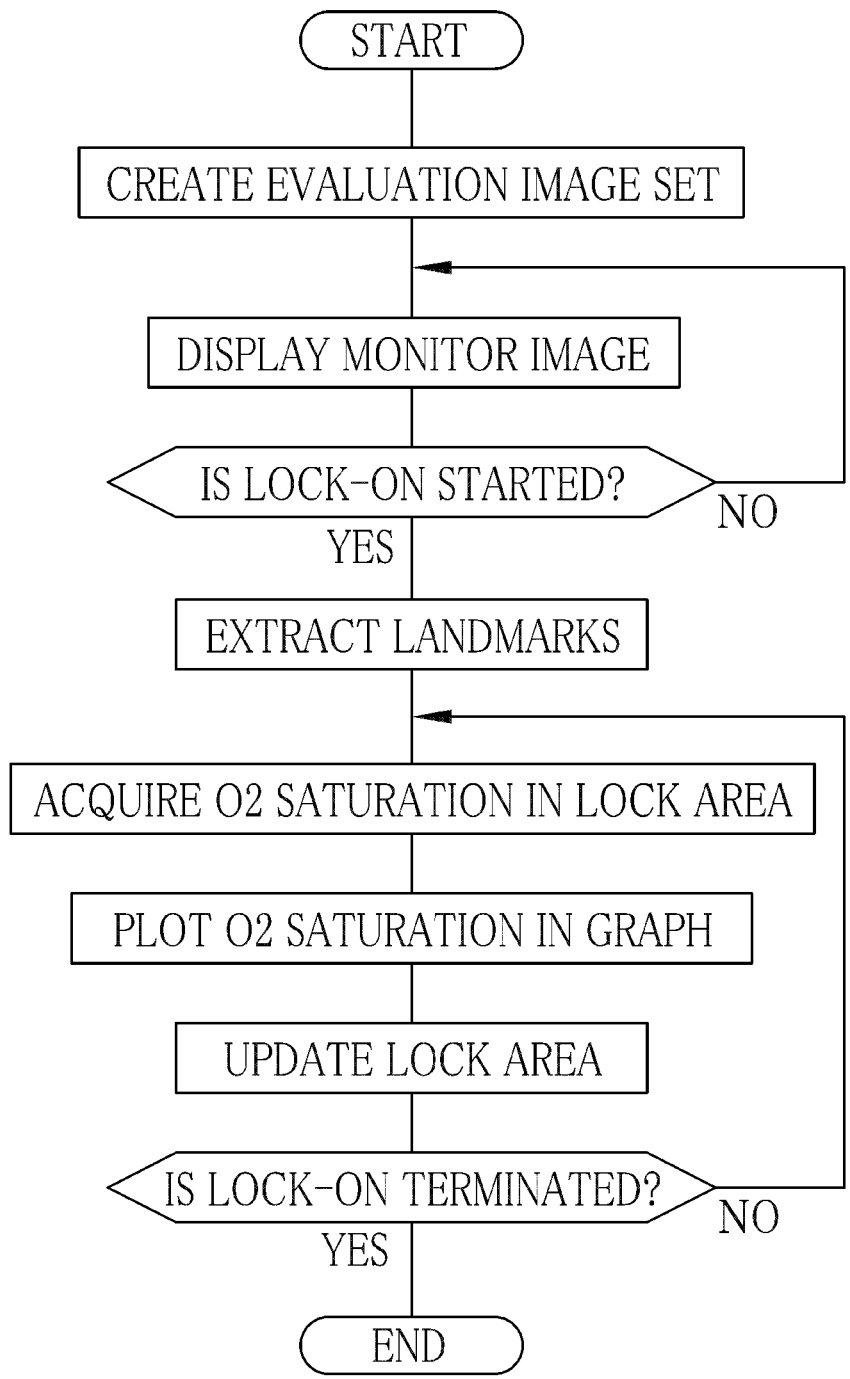
FIG. 15 is a flow chart illustrating a process of in vivo monitoring of the invention.

The operation of the embodiment is described now by referring to the flow chart in FIG. 15. The monitor mode for oxygen saturation is set by manually operating the selection switch 23 of the laparoscope. The measuring light with a center wavelength of 473 nm, and the white light generated by excitation of light with a center wavelength of 445 nm is emitted alternately with one another, and applied to an object in a body cavity. Object light is detected by the image sensor 60 with blue, green and red pixels. Thus, an evaluation image set inclusive of a special light mode image and a normal image is created, the special light mode image being formed after application of the measuring light, the normal image being formed after application of the white light. Note that control for creating an evaluation image set is repeated while the monitor mode is set.

At each time of creating an evaluation image set, the display panel 14 displays the monitor image 94 for in vivo monitoring. In the monitor image 94, the object image 92 appears as a normal image in the evaluation image set. The graph 93 beside the object image 92 expresses the oxygen saturation of the body tissue in a time sequential manner. While the monitor image 94 is displayed, the reference area 96 is indicated in the object image 92 before setting the lock area 98.

A doctor or operator observes the image on the display panel 14, and manipulates the input interface 15 and the head assembly of the guide tube 32 to place an object of interest of the body tissue in the reference area 96. He or she depresses the lock-on switch 19 when the object of interest enters the reference area 96. Thus, a region of the object of interest is determined as the lock area 98. Operation of the lock-on starts.

When the lock area 98 is set, the landmark points 100 are extracted from the first normal image of the first evaluation image set at the time of setting the lock area 98. Also, signal levels B1', G1' and R1' of the part image of the lock area 98 are extracted from the first special light mode image of the first evaluation image set. Signal levels B2', G2' and R2' of the part image of the lock area 98 are extracted from the first normal image.

When a signal level of the part image of the lock area 98 is determined, then the signal ratios B1'/G2' and R2'/G2' of the part image are determined by the ratio generator 89a. Then the arithmetic processor 89c obtains an oxygen saturation corresponding to the signal ratios B1'/G2' and R2'/G2' on the basis of the correlation stored in the correlation memory 89b. Thus, the oxygen saturation of the lock area 98 is acquired. The acquired oxygen saturation is plotted on the object image 92 in the monitor image 94 by the graph generator 86a.

Then plural landmark points are extracted from second normal image in a second evaluation image set created after the first evaluation image set. Landmark points, which are included in those in the second normal image and those in the first normal image and of which the feature value is equal, are specified. A movement amount M between the specified landmark points is obtained. A shift between the first and second normal images is obtained according to the movement amount M, so as to update the location of the lock area 98. An oxygen saturation of the part image of the lock area 98 of the updated location is measured, and plotted on the graph 93, in the manner similar to that described above.

For third, fourth, . . . , and nth evaluation image sets, the lock area 98 is updated similarly. The oxygen saturation is measured and plotted in the graph 93. The measurement and plotting of the oxygen saturation are repeated until the lock-on switch 19 is depressed next. Thus, the lock area 98 is displaced according to motion of the object of interest. The oxygen saturation of the lock area 98 is determined at each time of the motion. If there is a large shift in the object of interest, the change with time can be monitored for the oxygen saturation of the object of interest.

When the lock-on switch 19 is depressed again, the locked state is terminated for release. The measurement of the oxygen saturation of the lock area 98 is terminated. At the same time, the lock area 98 is deleted in the object image 92. The reference area 96 is displayed in the object image 92 again.

Figure 16:
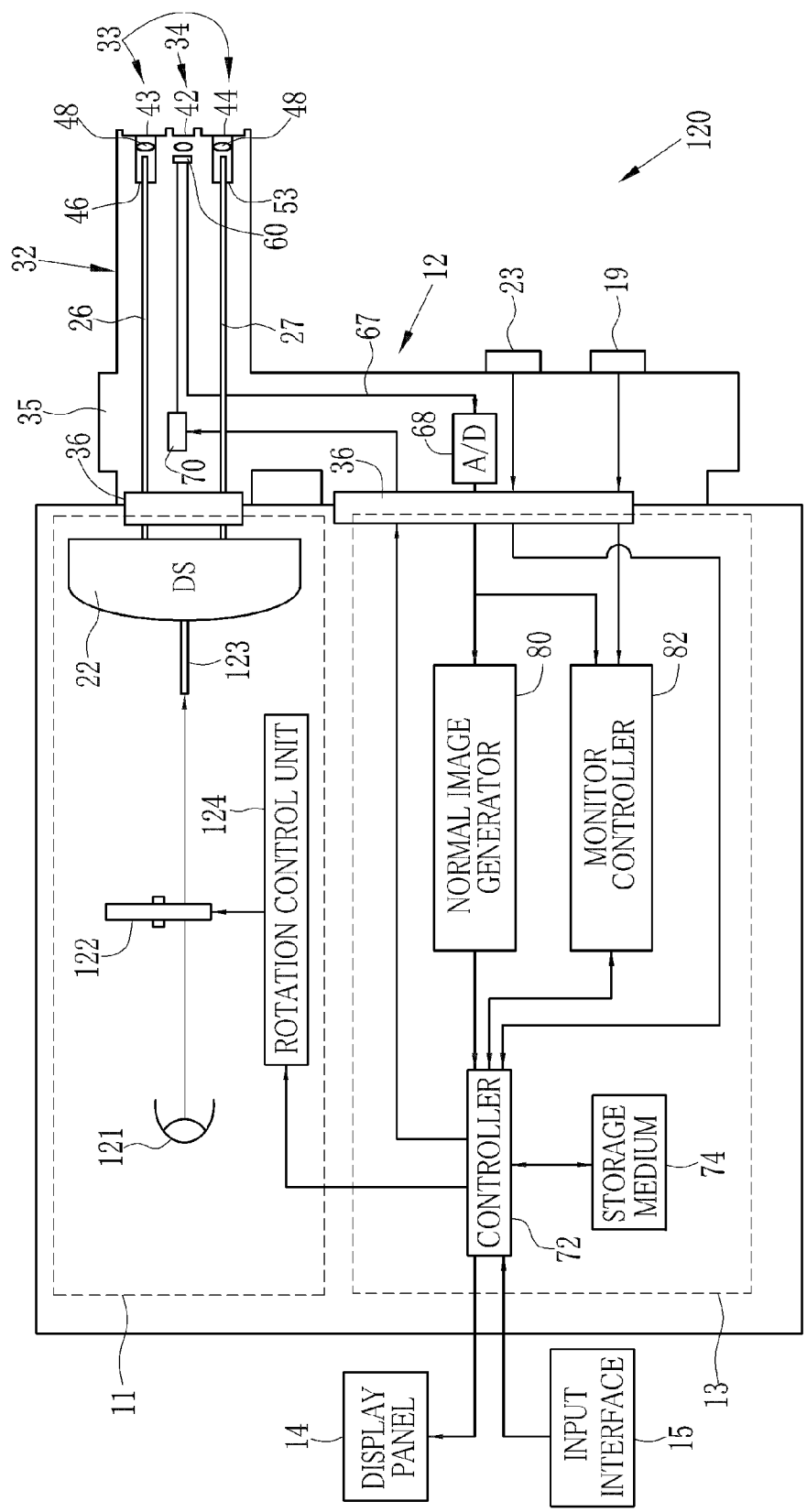
FIG. 16 is a block diagram illustrating another preferred laparoscope system.

In FIG. 16, another preferred laparoscope system 120 as tissue imaging system is illustrated. The illumination apparatus 11 has a structure of a rotatable filter wheel 122. Light from the filter wheel 122 is applied through the lighting units 46 and 53 toward a body cavity. Elements of the laparoscope system 120 similar to those of the laparoscope system 2 are designated with identical reference numerals.

The laparoscope system 120 includes a white light source 121 or broad band light source, the filter wheel 122, fiber optics 123 and a rotation control unit 124 in place of the laser light sources LD1 and LD2, the lighting control unit 20 and the optical coupler 21. The white light source 121, for example, a xenon light source, emits white light of spectral intensity of FIG. 17. The filter wheel 122 transmits a component of measuring light partially with a specific wavelength range included in the white light, or transmits white light fully. The fiber optics 123 receive the light transmitted by the filter wheel 122. The rotation control unit 124 controls the rotation of the filter wheel 122. The light incident upon the fiber optics 123 is distributed by the optical distributor 22 for two light paths. The light passes through the light guide devices 26 and 27, and is applied to an object of interest through the lighting units 46 and 53.

Figure 18:
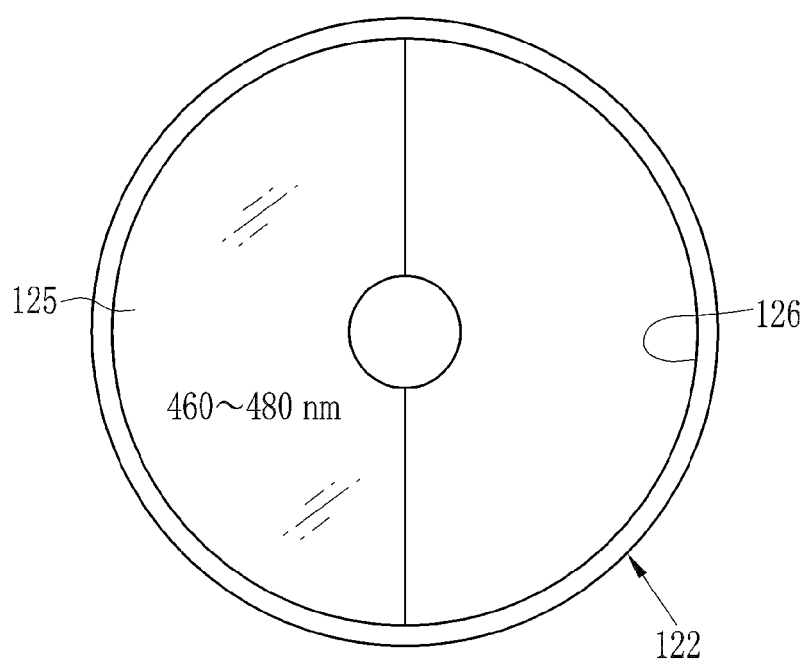
FIG. 18 is a front elevation illustrating a filter wheel.

In FIG. 18, the filter wheel 122 includes a narrow band filter 125 (blue) and a transmission region 126. The narrow band filter 125 passes measuring light of FIG. 4 partially with a wavelength range of 460-480 nm as a component in white light. The transmission region 126 passes the white light fully. When the filter wheel 122 rotates, the measuring light and white light is applied to a wall of the body cavity in an alternate manner. In a manner similar to the above embodiment, an image signal of a first frame is obtained upon application of the measuring light. An image signal of a second frame is obtained upon application of the white light. An evaluation image set is constituted by the image signals of those two frames, and is used for determining oxygen saturation of the part image of the lock area 98 in a manner similar to the above embodiment.

Figure 17:
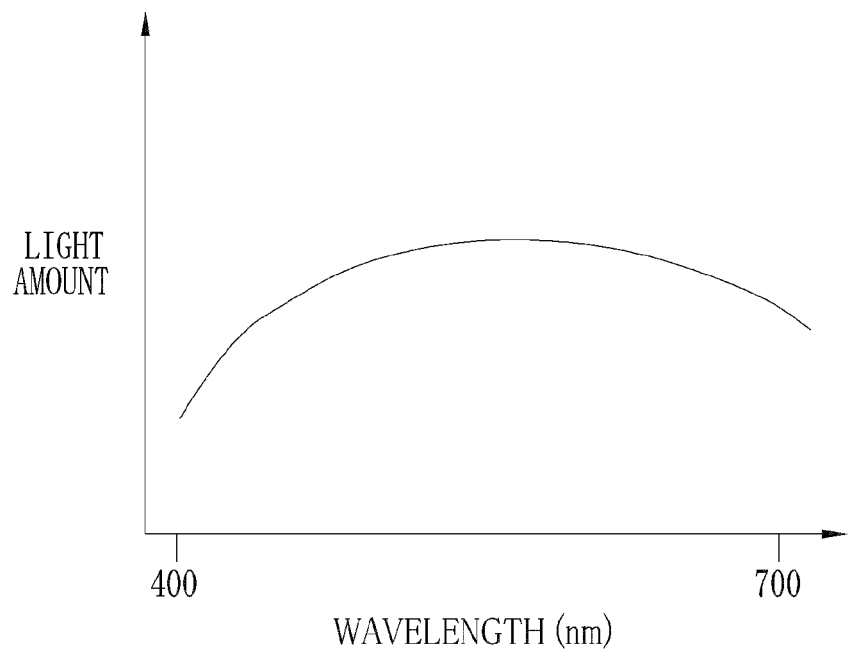
FIG. 17 is a graph illustrating spectral distribution of white light.

The white light according to the embodiment has spectral distribution of FIG. 17. A blue signal B2 of a normal image contains a component of light of a wavelength range of 400-530 nm. A green signal G2 of the normal image contains a component of light of a wavelength range of 540-580 nm. A red signal R2 of the normal image contains a component of light of a wavelength range of 590-700 nm.

Figure 19:
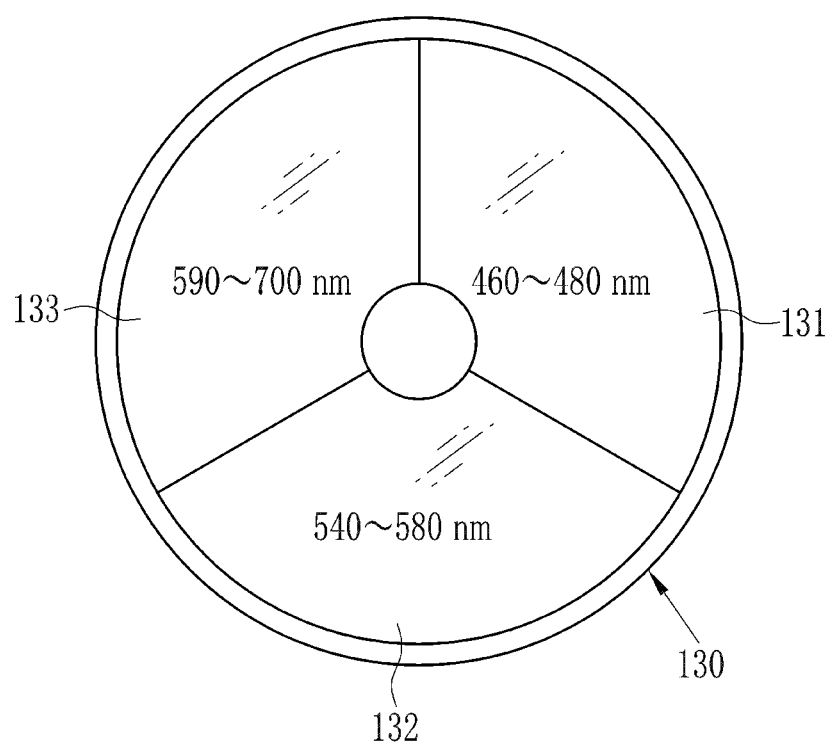
FIG. 19 is a front elevation illustrating another preferred filter wheel with three filters.

In FIG. 19, another preferred filter wheel 130 is illustrated in a structure different from the filter wheel 122. A first filter 131 (blue) in the filter wheel 130 passes a first light component in a wavelength range of 460-480 nm included in white light from the white light source 121. A second filter 132 (green) passes a second light component in a wavelength range of 540-580 nm included in the white light. A third filter 133 (red) passes a third light component in a wavelength range of 590-700 nm included in the white light. As the filter wheel 130 rotates, the first, second and third light components are applied to an object of interest.

When the filter wheel 130 is used, the image sensor 60 of a monochromatic type detects object light for imaging at each time that the first, second and third light components are transmitted and applied to the object. Thus, image signals of three frames are obtained in a condition with the first, second and third light components. Let a blue signal B be an image signal obtained after lighting with the first light component. Let a green signal G be an image signal obtained after lighting with the second light component. Let a red signal R be an image signal obtained after lighting with the third light component. Signal ratios for determining oxygen saturation are B/G and R/G. The ratio R/G corresponds to the ratio R2/G2 of the first embodiment. The ratio B/G corresponds to the ratio B1/G2 of the first embodiment.

Figure 20:
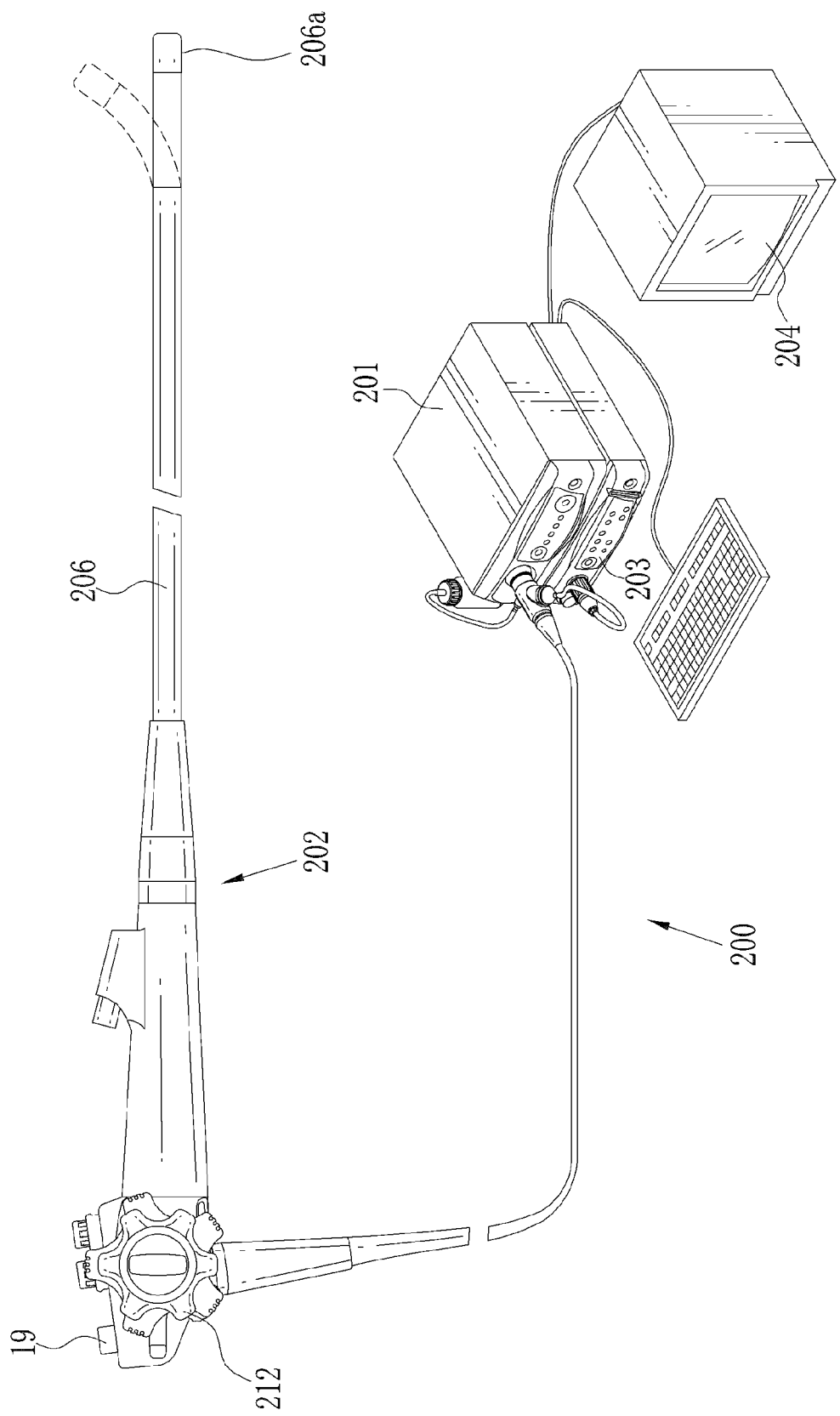
FIG. 20 is an explanatory view illustrating an endoscope system of the invention.

In the above embodiment, the medical instrument for use in the imaging system of the invention is the laparoscope. Furthermore, FIG. 20 illustrates another preferred embodiment in which the feature of the invention is used in an endoscope system 200 as tissue imaging system.

The endoscope system 200 includes an illumination apparatus 201, a processing apparatus 203, and a display panel 204 as display unit in the same manner as those in the laparoscope system 2. A gastrointestinal endoscope 202 includes an elongated tube 206 or guide tube, a head assembly 206a, four lighting units and an imaging unit. The lighting units apply measuring light and white light to a wall of a body cavity in the manner of the light emitter 33. The imaging unit images the wall of the body cavity in the manner of the imaging unit 34. Remaining portions of the endoscope 202 are constructed in the manner of the laparoscope 12.

Steering wheels 212 are rotatable for steering the head assembly 206a of the elongated tube 206 up and down and to the right and left. It is likely that a doctor or operator visually misses an object of interest when the head assembly 206a is steered. However, the lock area 98 is used for marking the object of interest as described heretofore, so that the object of interest will not be missed. Measurement of the oxygen content of the object of interest can be reliable in use of the endoscope 202.

In the above embodiments, the lock area is updated by use of the landmark points obtained by the edge detection. However, other parameters may be used for updating the lock area, for example, width, depth and shape of blood vessels.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. A tissue imaging system comprising:
    an imaging unit configured to create an object image with information of oxygen saturation of a blood vessel;
    an area determining unit configured to determine a lock area within said object image;
    a location updating unit configured to update a location of said lock area according to motion of said object at each time of creating a frame of said object image, said location updating unit executing:
        a landmark point extracting process to extract first landmark points from a first frame, and to extract second landmark points from a second frame created after creation of said first image, wherein said first and second landmark points are distinct from said lock area;
        a landmark point specifying process to specify part of said second landmark points whose feature value is equal to part of said first landmark points;
        a movement amount obtaining process to obtain a movement amount between said first and second landmark points whose feature value is equal; and
        a location changing process to change the location of said lock area according to said movement amount;
    a data acquisition unit configured to acquire said oxygen saturation in said lock area when said lock area is updated;
    a monitor image generating unit configured to generate a monitor image including acquired change information of said oxygen saturation; and
    a display unit configured to display said monitor image.

2. A tissue imaging system as defined in claim 1, wherein said first and second landmark points are extracted from a form of said blood vessel in said object.

3. A tissue imaging system as defined in claim 2, wherein said first and second landmark points are obtained by edge detection.

4. A tissue imaging system as defined in claim 1, wherein said object image created by said imaging unit is two spectral images of wavelength components of light of which an absorption coefficient is different between oxidized hemoglobin and reduced hemoglobin, and said data acquisition unit acquires said oxygen saturation of said lock area according to said two spectral images.

5. A tissue imaging system as defined in claim 1, wherein said monitor image generating unit generates a graph of said oxygen saturation changeable with time, and said monitor image includes said graph, and wherein said display unit displays a currently created frame of said object image within said monitor image together with said graph.

6. A tissue imaging system as defined in claim 1, further comprising an alarm device for generating an alarm signal if said oxygen saturation in said lock area becomes equal to or lower than a predetermined level.

7. A tissue imaging system as defined in claim 1, further comprising an illumination apparatus configured to apply narrow band light of a predetermined wavelength range and broad band light of a broad wavelength range alternately to said object;
    wherein said imaging unit is a color image sensor for imaging said object illuminated with said narrow band light and said broad band light.

8. A tissue imaging system as defined in claim 7, wherein said narrow band light has a wavelength range of 460-480 nm, and wherein said imaging unit obtains a special light mode image upon application of said narrow band light, and obtains a normal image upon application of said broad band light, as said object image.

9. A tissue imaging system as defined in claim 8, wherein said data acquisition unit including:
    a ratio generator configured to determine a first signal ratio of a blue signal of said special light mode image to a green signal of said normal image, and a second signal ratio of a red signal of said normal image to a green signal of said normal image;
    a correlation memory configured to store information of a correlation between said oxygen saturation and said first and second signal ratios; and
    an arithmetic processor configured to determine said oxygen saturation in said lock area by use of said correlation read from said correlation memory and said first and second signal ratios obtained by said ratio generator.

10. A tissue imaging system as defined in claim 1, further comprising an illumination apparatus configured to apply plural narrow band light components of wavelength ranges different from one another to said object successively one after another;
    wherein said imaging unit is a monochromatic image sensor for imaging said object illuminated with said narrow band light components.

11. A tissue imaging system as defined in claim 10, wherein said plural narrow band light components are a first light component in a wavelength range of 460-480 nm, a second light component in a wavelength range of 540-580 nm, and a third light component in a wavelength range of 590-700 nm, and wherein said imaging unit obtains a blue signal corresponding to said first light component, a green signal corresponding to said second light component, and a red signal corresponding to said third light component, as said object image.

12. A tissue imaging system as defined in claim 11, wherein said data acquisition unit including:
   a ratio generator configured to determine a first signal ratio of said blue signal to said green signal, and a second signal ratio of said red signal to said green signal;
   a correlation memory configured to store information of a correlation between said oxygen saturation and said first and second signal ratios; and
   an arithmetic processor configured to determine said oxygen saturation in said lock area by use of said correlation read from said correlation memory and said first and second signal ratios obtained by said ratio generator.

13. A tissue imaging system as defined in claim 1, wherein said object is present in an abdominal cavity, and said imaging unit is a laparoscope.

14. A tissue imaging system as defined in claim 1, wherein said object is present in a gastrointestinal tract, and said imaging unit is an endoscope.

15. An in vivo monitoring method comprising steps of:
   creating an object image with information of oxygen saturation of a blood vessel;
   determining a lock area within said object image;
   updating a location of said lock area according to motion of said object at each time of creating a frame of said object image, said updating step executing:
      extracting first landmark points from a first frame, and to extract second landmark points from a second frame created after creation of said first image, wherein said first and second landmark points are distinct from said lock area;
      specifying part of said second landmark points whose feature value is equal to part of said first landmark points;
      obtaining a movement amount between said first and second landmark points whose feature value is equal; and
      changing the location of said lock area according to said movement amount;
   acquiring said oxygen saturation in said lock area when said lock area is updated;
   generating a monitor image including acquired change information of said oxygen saturation; and
   displaying said monitor image.

16. An in vivo monitoring method as defined in claim 15, wherein said object image created by said creating step is two spectral images of wavelength components of light of which an absorption coefficient is different between oxidized hemoglobin and reduced hemoglobin, and in said acquiring step, said oxygen saturation of said lock area is acquired according to said two spectral images.

* * * * *